(12) United States Patent
Sherwood et al.

(10) Patent No.: US 11,819,277 B2
(45) Date of Patent: Nov. 21, 2023

(54) INTRAOCULAR PRESSURE SENSING MATERIAL, DEVICES, AND USES THEREOF

(71) Applicant: University of Florida Research Foundation, Inc., Gainesville, FL (US)

(72) Inventors: Mark B. Sherwood, Gainesville, FL (US); Peng Jiang, Gainesville, FL (US); Aaron David Webel, Columbia, MO (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 477 days.

(21) Appl. No.: 17/051,051

(22) PCT Filed: Jun. 20, 2019

(86) PCT No.: PCT/US2019/038193
§ 371 (c)(1),
(2) Date: Oct. 27, 2020

(87) PCT Pub. No.: WO2019/246370
PCT Pub. Date: Dec. 26, 2019

(65) Prior Publication Data
US 2021/0186326 A1 Jun. 24, 2021

Related U.S. Application Data

(60) Provisional application No. 62/687,614, filed on Jun. 20, 2018.

(51) Int. Cl.
*A61B 3/16* (2006.01)
*A61B 5/00* (2006.01)
*A61F 2/16* (2006.01)
*A61F 9/007* (2006.01)
*A61M 25/00* (2006.01)

(52) U.S. Cl.
CPC .............. *A61B 3/16* (2013.01); *A61B 5/0075* (2013.01); *A61B 5/686* (2013.01); *A61F 2/16* (2013.01); *A61F 9/00781* (2013.01); *A61F 2250/0081* (2013.01); *A61M 25/0045* (2013.01); *A61M 2205/584* (2013.01)

(58) Field of Classification Search
CPC ......... A61B 3/16; A61B 5/0075; A61B 5/686; A61F 2/16; A61F 9/00781; A61F 2250/0081; A61M 25/0045; A61M 2205/584
See application file for complete search history.

(56) References Cited

U.S. PATENT DOCUMENTS

| 3,422,535 A | 1/1969 | Johnson |
| 3,671,105 A | 6/1972 | Williams et al. |
| 4,125,319 A | 11/1978 | Frank et al. |
| 4,340,479 A | 7/1982 | Pall |
| 4,664,748 A | 5/1987 | Ueno et al. |
| 4,781,441 A | 11/1988 | Kanbe et al. |
| 4,810,633 A | 3/1989 | Bauer et al. |
| 5,147,716 A | 9/1992 | Bellus |
| 5,337,018 A | 8/1994 | Yamagishi |
| 5,429,743 A | 7/1995 | Geus et al. |
| 5,529,524 A | 6/1996 | Jones |
| 5,641,332 A | 6/1997 | Faber et al. |
| 5,753,014 A | 5/1998 | Van Rijn |
| 5,939,189 A | 8/1999 | Phillips et al. |
| 5,948,470 A | 9/1999 | Harrison et al. |
| 5,993,661 A | 11/1999 | Ruckenstein et al. |
| 6,044,981 A | 4/2000 | Chu et al. |
| 6,531,304 B1 | 3/2003 | Boennemann et al. |
| 6,565,763 B1 | 5/2003 | Asakawa et al. |
| 6,649,255 B1 | 11/2003 | Fain et al. |
| 6,881,582 B2 | 4/2005 | Ratogi et al. |
| 6,929,764 B2 | 8/2005 | Jiang et al. |
| 6,958,137 B2 | 10/2005 | Lee et al. |
| 7,351,470 B2 | 4/2008 | Draheim et al. |
| 7,630,589 B2 | 12/2009 | Kilic et al. |
| 7,691,325 B2 | 4/2010 | Chopra et al. |
| 7,889,954 B2 | 2/2011 | Sailor et al. |
| 9,233,883 B1 | 1/2016 | Rauscher et al. |
| 9,272,947 B2 | 3/2016 | Baca et al. |
| 10,189,967 B2 | 1/2019 | Jiang et al. |
| 10,700,225 B2 | 6/2020 | Wang et al. |
| 2003/0031438 A1 | 2/2003 | Kambe et al. |

(Continued)

FOREIGN PATENT DOCUMENTS

| CN | 103935057 A | 7/2014 |
| CN | 105036068 A | 11/2015 |

(Continued)

OTHER PUBLICATIONS

Khaw et al., "ABC of Eyes", BMJ, 328, 97-99, Jan. 10, 2004 (Year: 2004).*

(Continued)

*Primary Examiner* — Eric F Winakur
*Assistant Examiner* — Jonathan Drew Moroneso
(74) *Attorney, Agent, or Firm* — Thomas|Horstemeyer LLP

(57) ABSTRACT

Described herein are eye implants that can include a pressure-responsive material that can be capable of changing color in response to pressure exerted on it. Also described here are methods of implanting and using the eye implants described herein to monitor intraocular pressure in a subject. The pressure-responsive material can be used to diagnose and monitor human or animal subjects.

19 Claims, No Drawings

(56) References Cited

U.S. PATENT DOCUMENTS

| | | |
|---|---|---|
| 2004/0131779 A1 | 7/2004 | Haubrich et al. |
| 2004/0131799 A1 | 7/2004 | Arsenault et al. |
| 2004/0184948 A1 | 9/2004 | Rakow et al. |
| 2005/0147807 A1 | 7/2005 | Haas et al. |
| 2006/0052470 A1* | 3/2006 | Grech .................. A61K 6/891 |
| | | 522/74 |
| 2006/0137462 A1 | 6/2006 | Divigalpitiya et al. |
| 2007/0036653 A1 | 2/2007 | Bak et al. |
| 2007/0156079 A1 | 7/2007 | Brown |
| 2007/0206270 A1 | 9/2007 | Iwamatsu et al. |
| 2008/0006574 A1 | 1/2008 | Ramaswamy et al. |
| 2008/0027199 A1 | 1/2008 | Mazurek et al. |
| 2008/0108142 A1 | 5/2008 | Hall et al. |
| 2008/0185498 A1 | 8/2008 | Purdy et al. |
| 2008/0233418 A1 | 9/2008 | Krueger |
| 2008/0309923 A1 | 12/2008 | Falk |
| 2009/0034051 A1 | 2/2009 | Arsenault et al. |
| 2009/0274873 A1 | 11/2009 | Shinotsuka |
| 2010/0051561 A1 | 3/2010 | Lee |
| 2010/0058844 A1 | 3/2010 | Lin et al. |
| 2010/0068168 A1 | 3/2010 | Song et al. |
| 2010/0069726 A1 | 3/2010 | Levinson |
| 2010/0125113 A1 | 5/2010 | Xiao et al. |
| 2010/0150511 A1 | 6/2010 | Arsenault et al. |
| 2010/0155325 A1 | 6/2010 | Zhang et al. |
| 2010/0188732 A1 | 7/2010 | Akashi et al. |
| 2010/0216310 A1 | 8/2010 | Metz et al. |
| 2010/0218716 A1 | 9/2010 | Havens et al. |
| 2010/0235107 A1 | 9/2010 | Fukumura et al. |
| 2010/0244169 A1 | 9/2010 | Maeda et al. |
| 2010/0315703 A1 | 12/2010 | Purdy et al. |
| 2011/0019277 A1 | 1/2011 | Sager et al. |
| 2011/0097814 A1 | 4/2011 | Bommarito et al. |
| 2011/0111173 A1 | 5/2011 | Ogawa et al. |
| 2011/0140106 A1 | 6/2011 | Forbes |
| 2011/0194261 A1 | 8/2011 | Tanaka et al. |
| 2011/0233476 A1 | 9/2011 | Arsenault |
| 2011/0255035 A1 | 10/2011 | Wu |
| 2012/0051489 A1 | 3/2012 | Varanasi et al. |
| 2012/0073388 A1 | 3/2012 | Chibante |
| 2012/0074612 A1 | 3/2012 | Scrivens et al. |
| 2012/0152338 A1 | 6/2012 | Ha et al. |
| 2012/0225517 A1 | 9/2012 | Zhang et al. |
| 2012/0262789 A1 | 10/2012 | Xie et al. |
| 2012/0281292 A1 | 11/2012 | Baca et al. |
| 2012/0293802 A1 | 11/2012 | Ozin et al. |
| 2012/0313205 A1 | 12/2012 | Haddad et al. |
| 2012/0321810 A1 | 12/2012 | Tebby et al. |
| 2013/0078750 A1 | 3/2013 | Yeo et al. |
| 2013/0199995 A1 | 8/2013 | Jiang et al. |
| 2013/0215513 A1 | 8/2013 | Liang et al. |
| 2013/0222881 A1 | 8/2013 | Aizenberg et al. |
| 2013/0258483 A1 | 10/2013 | Pett et al. |
| 2013/0320467 A1 | 12/2013 | Buchanan et al. |
| 2013/0340824 A1 | 12/2013 | Oh et al. |
| 2014/0017145 A1 | 1/2014 | Aizenberg et al. |
| 2014/0106468 A1 | 4/2014 | Boersma |
| 2014/0166100 A1 | 6/2014 | Watanabe et al. |
| 2014/0319524 A1 | 10/2014 | Phillips et al. |
| 2015/0035269 A1 | 2/2015 | Hooper et al. |
| 2015/0157453 A1 | 6/2015 | Nazinzadeh et al. |
| 2015/0276989 A1 | 10/2015 | Han et al. |
| 2016/0032141 A1 | 2/2016 | Maghsoodi et al. |
| 2016/0254395 A1 | 9/2016 | Jiang et al. |
| 2016/0326334 A1 | 11/2016 | Jiang et al. |
| 2017/0209045 A1 | 7/2017 | Choo et al. |
| 2017/0215790 A1 | 8/2017 | Levinson et al. |
| 2017/0225395 A1 | 8/2017 | Boydston et al. |
| 2017/0271259 A1 | 9/2017 | Hotta et al. |

FOREIGN PATENT DOCUMENTS

| | | |
|---|---|---|
| EP | 0341675 A2 | 11/1989 |
| WO | 9820388 A1 | 5/1998 |
| WO | 2000010934 A1 | 3/2000 |
| WO | 02073699 A3 | 11/2002 |
| WO | 2007070486 A2 | 6/2007 |
| WO | 2008060322 A2 | 5/2008 |
| WO | 2010007853 A1 | 1/2010 |
| WO | 2015066337 A1 | 5/2015 |
| WO | 2018213570 A2 | 11/2018 |

OTHER PUBLICATIONS

Wang et al., "Photonic Crystal Structures with Tunable Structure Color as Colorimetric Sensors", sensors, 13, 4192-4213, published Mar. 28, 2013 (Year: 2013).*

Aksoy, Gökhan, et al. "Effect of various treatment and glazing (coating) techniques on the roughness and wettability of ceramic dental restorative surfaces." Colloids and surfaces B: Biointerfaces 53.2 (2006): 254-259.

Al-Marzok, Maan; et al. "The effect of the surface roughness of porcelain on the adhesion of oral Streptococcus mutans." J Contemp Dent Pract 10.6 (2009): E017-24.

Bartlett, D. W., et al. "The association of tooth wear, diet and dietary habits in adults aged 18-30 years old." Journal of dentistry 39.12 (2011): 811-816.

Butler, Craig J., et al. "Effect of fluoride and 10% carbamide peroxide on the surface roughness of low-fusing and ultra low-fusing porcelain." The Journal of prosthetic dentistry 92.2 (2004): 179-183.

Ccahuana, Vanessa ZS, et al. "Surface degradation of glass ceramics after exposure to acidulated phosphate fluoride." Journal of Applied Oral Science 18.2 (2010): 155-165.

Creugers, Nico HJ; et al. "A meta-analysis of durability data on conventional fixed bridges." Community Dentistry and Oral Epidemiology 22.6 (1994): 448-452.

Drummond, J. L., D; et al. "Physiological aging of an all-ceramic restorative material." Dental Materials 7.2 (1991): 133-137.

Esquivel-Upshaw, Josephine, et al. "Randomized, controlled clinical trial of bilayer ceramic and metal-ceramic crown performance." Journal of Prosthodontics: Implant, Esthetic and Reconstructive Dentistry 22.3 (2013): 166-173.

Esquivel-Upshaw, Josephine F., et al. "Resistance to staining, flexural strength, and chemical solubility of core porcelains for all-ceramic crowns." International Journal of Prosthodontics 14.3 (2001).

Esquivel-Upshaw, Josephine F., et al. "In Vivo Wear of Enamel by a Lithia Disilicate—Based Core Ceramic Used for Posterior Fixed Partial Dentures: First-Year Results." International Journal of Prosthodontics 19.4 (2006).

Esquivel-Upshaw, J. F., et al. "Surface degradation of dental ceramics as a function of environmental pH." Journal of dental research 92.5 (2013): 467-471.

Fischer, H.; et al. "Effect of surface roughness on flexural strength of veneer ceramics." Journal of Dental Research 82.12 (2003): 972-975.

Flannery, Anthony F., et al. "PECVD silicon carbide as a chemically resistant material for micromachined transducers." Sensors and Actuators A: Physical 70.1-2 (1998): 48-55.

Zhang, Haixia, et al. "Application of PECVD SiC in glass micromachining." Journal of Micromechanics and Microengineering 17.4 (2007): 775.

Heintze, Siegward D; et al. "Survival of zirconia-and metal-supported fixed dental prostheses: a systematic review." International Journal of Prosthodontics 23.6 (2010).

Herrmann, M., et al. "Corrosion of silicon nitride materials in acidic and basic solutions and under hydrothermal conditions." Journal of the European Ceramic Society 23.4 (2003): 585-594.

Herrmann, M. "Corrosion of silicon nitride materials in aqueous solutions." Journal of the American Ceramic Society 96.10 (2013): 3009-3022.

Ogawa, Yudai, et al. "Organic transdermal iontophoresis patch with built-in biofuel cell." Advanced healthcare materials 4.4 (2015): 506-510.

Kukiattrakoon, Boonlert; et al. "Vicker's microhardness and energy dispersive x-ray analysis of fluorapatite-leucite and fluorapatite

(56) References Cited

OTHER PUBLICATIONS ceramics cyclically immersed in acidic agents." Journal of oral science 51.3 (2009): 443-450.
Kukiattrakoon, Boonlert; et al. "The effect of acidic agents on surface ion leaching and surface characteristics of dental porcelains." The journal of prosthetic dentistry 103.3 (2010): 148-162.
Kukiattrakoon, Boonlert; et al. "Degradability of fluorapatite-leucite ceramics in naturally acidic agents." Dental materials journal (2010): 1008310070-1008310070.
Kukiattrakoon, Boonlert; et al. "Chemical durability and microhardness of dental ceramics immersed in acidic agents." Acta Odontologica Scandinavica 68.1 (2010): 1-10.
Kukiattrakoon, Boonlert; et al. "Effect of acidic agents on surface roughness of dental ceramics." Dental research journal 8.1 (2011): 6.
Milleding, Percy, et al. "Surface energy of non-corroded and corroded dental ceramic materials before and after contact with salivary proteins." European journal of oral sciences 107.5 (1999): 384-392.
Miyazaki, Takashi, et al. "Current status of zirconia restoration." Journal of prosthodontic research 57.4 (2013): 236-261.
Pinto, Marcelo M., et al. "Influence of pH on slow crack growth of dental porcelains." dental materials 24.6 (2008): 814-823.
Preis, Verena, et al. "Wear performance of dental ceramics after grinding and polishing treatments." Journal of the mechanical behavior of biomedical materials 10 (2012): 13-22.
Raigrodski, Ariel J.; et al. "The safety and efficacy of anterior ceramic fixed partial dentures: a review of the literature." The journal of prosthetic dentistry 86.5 (2001): 520-525.
Rosenstiel, S. F., et al. "Strength of a dental glass-ceramic after surface coating." Dental Materials 9.4 (1993): 274-279.
Sailer, Irena, et al. "A systematic review of the survival and complication rates of all-ceramic and metal-ceramic reconstructions after an observation period of at least 3 years. Part II: fixed dental prostheses." Clinical oral implants research 18 (2007): 86-96.
Salido, María P., et al. "Prospective clinical study of zirconia-based posterior four-unit fixed dental prostheses: four-year follow-up." International Journal of Prosthodontics 25.4 (2012).
Scurria, Mark S.; et al. "Meta-analysis of fixed partial denture survival: prostheses and abutments." The Journal of prosthetic dentistry 79.4 (1998): 459-464.
Karrock, Torben; et al. "Pressure sensor based on flexible photonic crystal membrane." Biomedical optics express 6.12 (2015): 4901-4911.
International Search Report for PCT/US19/38193 dated Sep. 5, 2019.
Velev, O. D.; et al. Materials Fabricated by Micro- and Nanoparticle Assembly—the Challenging Path from Science to Engineering. Adv. Mater. 2009, 21, 1897-1905.
"Light" Wikipedia https://en.wikipedia.orgiwiindex.php?title=Light&oldid=797818857 (accessed Feb. 22, 2019).
"Using polyimide tape to mask against reactive-ion etching" Tech Briefs, 2002 (accessed Feb. 22, 2019).
A. Deak, B. Bancsi, A.L. Toth, A.L. Kovacs, Z. Horvolgyi, "Complex Langmuir-Blodgett films from silica nanoparticles: An optical spectroscopy study", Colloid Surf. A 278 (2006) 10-16.
A. Deak, I. Szekely, E. Kalman, Z. Keresztes, A.L. Kovacs, Z. Horvolgyi, "Nanostructured silica Langmuir-Blodgett films with antireflective properties prepared on glass substrates", Thin Solid Films 484 (2005) 310-317.
A. Gombert, B. Blasi, C. Buhler, P. Nitz, J. Mick, W. Hossfeld, M. Niggemann, "Some application cases and related manufacturing techniques for optically functional microstructures on large areas", Opt. Eng. 43 (2004) 2525-2533.
A. Gombert, W. Glaubitt, K. Rose, J. Dreibholz, B. Bläsi, A. Heinzel, D. Sporn, W. Döll, V. Wittwer, "Subwavelength-structured antireflective surfaces on glass", Thin Solid Films 351 (1999) 73-78.
Zhao, Y.; et al Bio-Inspired Variable Structural Color Materials. Chem. Soc. Rev. 2012, 41, 3297-3317.

Aguirre, C. I.; et al. Tunable Colors in Opals and Inverse Opal Photonic Crystals. Adv. Funct. Mater. 2010, 20, 2565-2578.
Arsenault et al., "From colour fingerprinting to the control of photoluminescence in elastic photonic crystals", nature materials 2006, 5: 179-184.
Asher et al., "Photonic Crystal Carbohydrate Sensors: Low Ionic Strength Sugar Sensing", J. Am. Chem. Soc. 2003, 125: 3322-3329.
B.-T. Liu, Y.-T. Teng, R.-H. Lee, W.-C. Liaw, C.-H. Hsieh, "Strength of the interactions between light-scattering particles and resins affects the haze of anti-glare films", Colloid Surf. A 389 (2011) 138-143.
B.E. Yoldas, D.P. Partlow, "Formation of Broad Band Antireflective Coatings on Fused Silica for High Power Laser Applications", Thin Solid Films 129 (1985) 1-14.
B.G. Prevo, E.W. Hon, O.D. Velev, "Assembly and characterization of colloid-based antireflective coatings on multicrystalline silicon solar cells", J. Mater. Chem. 17 (2007) 791-799.
B.G. Prevo, O.D. Velev, "Controlled, Rapid Deposition of Structured Coatings from Micro- and Nanoparticle Suspensions", Langmuir 20 (2004) 2099-2107.
B.T. Liu, W.D. Yeh, "Antireflective surface fabricated from colloidal silica nanoparticles", Colloid Surf. A 356 (2010) 145-149.
B.T. Liu, W.D. Yeh, "Reflective properties of nanoparticle-arrayed surfaces", Thin Solid Films 518 (2010) 6015-6021.
B.T. Liu; et al. "A novel method to control inner and outer haze of an anti-glare film by surface modification of light-scattering particles", J. Colloid Interf. Sci. 350 (2010) 421-426.
Behl et al., "Multifunctional Shape-Memory Polymers", Adv. Mater. 2010, 22: 3388-3410.
Bertone et al., "Thickness Dependence of the Optical Properties of Ordered Silica-Air and Air-Polymer Photonic Crystals", Physical Review Letters 1999, 83, 2: 300-303.
Boyle, B. M.; et al. Structural Color for Additive Manufacturing: 3d-Printed Photonic Crystals from Block Copolymers. ACS Nano 2017, 11, 3052-3058.
Burgess et al., "Structural colour in colourimetric sensors and indicators", Journal of Materials Chemistry C 2013, 1: 6075-6086.
C. Heine, R.H. Morf, "Submicrometer gratings for solar energy applications", Appl. Opt. 34 (1995) 2476-2482.
C. Yakacki, "Shape-Memory and Shape-Changing Polymers", Polymer Reviews, 2013, 53: 1-5.
C.M. Kennemore Iii, U.J. Gibson, "Ion beam processing for coating MgF2 onto ambient temperature substrates", Appl. Opt. 23 (1984) 3608-3611.
C.S. Thompson, R.A. Fleming, M. Zou, "Transparent self-cleaning and antifogging silica nanoparticle films" Sol Energ Mater Sol C 115 (2013) 108-113.
Cansizoglu, H; et al. "Optical absorption properties of semiconducting nanostructures with different shapes" Advanced Optical Materials 2013, 1, 156-166. (Year: 2013).
Cao, Z; et al. "Study on the impact of silicon doping level on the trench profile using metal-assisted chemical etching" 2016, vol. 12,742-746.-1211.
Chan et al., "Mechanochromic Photonic Gels", Advanced Materials 2013, 25: 3934-3947.
Chen; et al. "Directed water shedding on high-aspect-ratio shape memory polymer micropillar arrays" Advanced Materials, 2014, pp. 1283-1288, vol. 26, doi: 10.1002/adma.201304030.
Cho, Y.; et al. Elastoplastic Inverse Opals as Power-Free Mechanochromic Sensors for Force Recording. Adv. Funct. Mater. 2015, 25, 6041-6049.
Cui et al., "Inverse Opal Spheres Based on Polyionic Liquids as Functional Microspheres with Tunable Optical Properties and Molecular Recognition Capabilities", Angew. Chem. Int. Ed. 2014, 53: 3844-3848.
D. Chen, "Anti-reflection (AR) coatings made by sol-gel processes: A review", Sol. Energ. Mater. Sol. C. 68 (2001) 313-336.
D. Lee, M.F. Rubner, R.E. Cohen, "All-Nanoparticle Thin-Film Coatings", Nano Lett. 6 (2006) 2305-2312.
D. Lee, Z. Gemici, M.F. Rubner, R.E. Cohen, "Multilayers of Oppositely Charged SiO2 Nanoparticles: Effect of Surface Charge on Multi9layer Assembly", Langmuir 23 (2007) 8833-8837.

(56) References Cited

OTHER PUBLICATIONS

D.G. Stavenga; et al. "Light on the moth-eye corneal nipple array of butterflies", Proc. R. Soc. B 273 (2006) 661-667.
Dangla, R.; et al. Microchannel Deformations Due to Solvent-Induced Pdms Swelling. Lab Chip 2010, 10, 2972-2978.
Ding et al., "Morphology and Water Vapor Permeability of Temperature-Sensitive Polyurethanes", Journal of Applied Polymer Science, (2008) vol. 107: 4061-4069.
Ding, T.; et al. Revealing Invisible Photonic Inscriptions: Images from Strain. ACS Appl. Mater. Interfaces 2015, 7, 13497-13502.
Du et al., "Solvent induced shape recovery of shape memory polymer based on chemically cross-linked poly(vinyl alcohol)", Soft Matter, 2010, 6: 3370-3376.
E. Metwalli, D.; et al. "Surface characterizations of mono-, di-, and tri-, aminosilane treated glass substrates", J. Colloid Interf. Sci. 298 (2006) 825-831.
Fang et al., "Reconfigurable photonic crystals enabled by pressure-responsive shape-memory polymers", Nature Communications 2015: 1-8.
Fang, Y.; et al. Chromogenic Photonic Crystals Enabled by Novel Vapor-Responsive Shape Memory Polymers. Adv. Mater. 2015, 27, 3696-3704.
Felton et al., Soft Matter "Self-folding with shape memory composites", Soft Matter, 2013, 9, 7688-7694.
Fenzl et al., "Photonic Crystals for Chemical Sensing and Biosensing", Angewandte Chemie Ed. 2015, 53: 3318-3335.
Witt, Kendhl Kate. "Optical Sensors for the Analysis of Alcohols in Fuels." (2016).
Woo et al., Preparation and characterization of three dimensionally ordered macroporous Li4Ti5O12 anode for lithium batteries, Electrochimica Acta 2007, 53(1): 79-82.
Yue et al., "Mechano-actuated ultrafast full-colour switching in layered photonic hydrogels", nature communications 2014: 1-8.
X. Li, O. Niitsoo, A. Couzis, "Electrostatically driven adsorption of silica nanoparticles on functionalized surfaces", J. Colloid Interf. Sci. 394 (2013) 26-35.
X. Li, O. Niitsoo, A. Couzis, "Experimental studies on irreversibility of electrostatic adsorption of silica nanoparticles at solid-liquid interface", J. Colloid Interf. Sci. 420 (2014) 50-56.
X.T. Zhang, O. Sato, M. Taguchi, Y. Einaga, T. Murakami, A. Fujishima, "Self-Cleaning Particle Coating with Antireflection Properties", Chem. Mater. 17 (2005) 696-700.
Xie et al., "Encoding Localized Strain History Through Wrinkle Based Structural Colors", Advanced Materials 2010, 22: 4390-4394.
Xu et al., "Deformable, Programmable, and Shape-Memorizing Micro-Optics", Advanced Functional Materials 2013, 23: 3299-3306.
Xue et al., "Synthesis and characterization of elastic star shape-memory polymers as self-expandable drug-eluting stents", Journal of Materials Chemistry 2012, 22: 7403-7411.
Y. Masuda, M. Itoh, T. Yonezawa, K. Koumoto, "Low-Dimensional Arrangement of SiO2 Particles", Langmuir 18 (2002) 4155-4159.
Y. Zhao, J.S. Wang, G.Z. Mao, "Colloidal subwavelength nanostructures for antireflection optical coatings", Opt. Lett. 30 (2005) 1885-1887.
Yakacki et al., "Shape-Memory Polymers for Biomedical Applications", Adv. Polym. Sci. 2010, 226: 147-175.
Yakacki et al., "Unconstrained recovery characterization of shape-memory polymer networks for cardiovascular applications", ScienceDirect, Biomaterials 2007, 28: 2255-2263.
Yakacki, Christopher M., et al. "Impact of shape-memory programming on mechanically-driven recovery in polymers." Polymer 52.21 (2011): 4947-4954.
Yang et al., "From Metastable Colloidal Crystalline Arrays to Fast Responsive Mechanochromic Photonic Gels: An Organic Gel for Deformation-Based Display Panels", Adv. Funct. Mater. 2014, 24: 3197-3205.
J. D. Joannopoulos, R. D. Meade, J. N. Winn, Photonic Crystals: Molding the Flow of Light, Princeton University Press, 135 pages.

A. Luque, S. Hegedus, Handbook of Photovoltaic Science and Engineering. John Wiley & Sons, West Sussex, 2003, 115 pages.
A. Lendlein, "Shape-Memory Polymers", Advances in Polymer Science 226, Springer, New York, NY 2010, 1-209.
H.A. Macleod, Thin-Film Optical Filters. Third ed., Institute of Physics Publishing, Bristol, 2001, 666 pages.
Gregg, S. J.; et al. Adsorption, Surface Area and Porosity. 2nd ed.; Academic Press Inc.: London, 1982.
Fudouzi et al., "Colloidal Crystals with Tunable Colors and Their Use as Photonic Papers", Langmuir 2003, 19: 9653-9660.
G. Zhou, J. He, J. "Antireflective coatings on Fresnel lenses by spin-coating of solid silica nanoparticles", Nanosci. Nanotechnol. 13 (2013) Abstract.
G.M. Nogueira, D. Banerjee, R.E. Cohen, M.F. Rubner, "Spray-Layer-by-Layer Assembly Can More Rapidly Produce Optical-Quality Multistack Heterostructures", Langmuir 27 (2011) 7860-7867.
Ge et al., "Highly Tunable Superparamagnetic Colloidal Photonic Crystals", Angew. Chem. Int. Ed. 2007, 46: 7428-7431.
Ge et al., "Rewritable Photonic Paper with Hygroscopic Salt Solution as Ink", Advanced Materials 2009, 21: 4259-4264.
Ge, J. P.; et al. Responsive Photonic Crystals. Angew. Chem. Int. Ed. 2011, 50, 1492-1522.
Gemici et al., "Targeted Functionalization of Nanoparticle Thin Films via Capillary Condensation", Nano Letters 2009, 9, 3: 1064-1070.
Yue et al., "Lamellar Hydrogels with High Toughness and Ternary Tunable Photonic Stop-Band", Advanced Materials 2013, 25: 3106-3110.
Grigoras et al., Fabrication of porous membrane filter from p-type silicon, Physica Status Solidi (a) 202(8): 1624-1628.
Gu et al., "Water-triggered shape memory of multiblock thermoplastic polyurethanes (TPUs)", RSC Adv. 2013, 3: 15783-15791.
Gugliuzza et al., "A review on membrane engineering for innovation in wearable fabrics and protective textiles", Journal of Membrane Science 446(2013): 350-375.
H. Fudouzi, M. Kobayashi, N. Shinya, "Assembly of Microsized Colloidal Particles on Electrostatic Regions Patterned through Ion Beam Irradiation", Langmuir 18 (2002) 7648-7652.
H. Jiang, K. Yu, Y.C. Wang, "Antireflective structures via spin casting of polymer latex", Opt. Lett. 32 (2007) 575-577.
H. Nagel, A. Metz, R. Hezel, "Porous SiO2 films prepared by remote plasma-enhanced chemical vapour deposition—a novel antireflection coating technology for photovoltaic modules", Sol. Energ. Mater. Sol. C. 65 (2001) 71-77.
H. Shimomura, Z. Gemici, R.E. Cohen, M.F. Rubner, "Layer-by-Layer-Assembled High-Performance Broadband Antireflection Coatings", ACS Appl. Mater. Interface 2 (2010) 813-820.
H.Y. Koo, D.K. Yi, S.J. Yoo, D.Y. Kim, "A Snowman-like Array of Colloidal Dimers for Antireflecting Surfaces**", Adv. Mater. 16 (2004) 274-277.
Habault et al., "Light-triggered self-healing and shape-memory polymers", Chem. Soc. Rev. 2013, 42: 7244-7256.
Han et al., "Full Color Tunable Photonic Crystal from Crystalline Colloidal Arrays with an Engineered Photonic Stop-Band", Adv. Mater. 2012, 24,: 6438-6444.
Han, H; et al. "Metal-assisted chemical etching of silicon and nanotechnology applications" ScienceDirect 2014, 9, 271-304.
Yoon, B.; et al, Recent Functional Material Based Approaches to Prevent and Detect Counterfeiting. J. Mater. Chem. C 2013, 1, 2388-2403.
Ye et al., "Invisible Photonic Prints Shown by Deformation", Advanced Functional Materials 2014, 24: 6430-6438.
Hatton et al., "Assembly of large-area, highly ordered, crack-free inverse opal films", PNAS 2010, vol. 107, 23: 10354-10359.
Heo, Y.; et al. Lithographically Encrypted Inverse Opals for Anti-Counterfeiting Applications. Small 2016, 12, 3819-3826.
Heuwers et al., "Shape-Memory Natural Rubber: An Exceptional Material for Strain and Energy Storage", Macromolecular Chemistry and Physics 2013, 214: 912-923.
Heuwers et al., "Stress-Induced Stabilization of Crystals in Shape Memory Natural Rubber", Macromolecular Rapid Communications 2013, 34: 180-184.

(56) References Cited

OTHER PUBLICATIONS

Holtz et al., "Polymerized colloidal crystal hydrogel films as intelligent chemical sensing materials", Nature 1997, 389: 829-832.
Huang et al., "Water-driven programmable polyurethane shape memory polymer: Demonstration and mechanism", Applied Physics Letters 2005, 86: 1-3.
Huang, Z; et al. "Metal-Assisted chemical etching of silicon: a review" Advanced Materials 2011, 23, 285-308.
International Search Report and Written Opinion for PCT/US2014/063163 dated Jun. 25, 2015.
International Search Report and Written Opinion issued in PCT/US2017/046886 dated Oct. 20, 2017.
International Search Report and Written Opinion dated Jun. 26, 2012 for PCT Patent Application No. PCT/US2011/057484.
International Search Report for International Application No. PCT/US2018/033173, dated Nov. 21, 2018.
International Search Report for International Application No. PCT/US2019/017862, dated Jan. 21, 2020.
International Search Report for PCT/US2018/066234 dated Mar. 25, 2019.
International Search Report for PCT/US2018/066349 dated Mar. 15, 2019.
International Search Report for PCT/US2018/066353 dated Mar. 15, 2019.
Ionov, Leonid. "Soft microorigami: self-folding polymer films." Soft Matter 7.15 (2011): 6786-6791.
J. Aizenberg, P.V. Braun, P. Wiltzius, "Patterned Colloidal Deposition Controlled by Electrostatic and Capillary Forces", Phys. Rev. Lett. 84 (2000) 2997-3000.
J. Tien, A. Terfort, G.M. Whitesides, "Microfabrication through Electrostatic Self-Assembly", Langmuir 13 (1997) 5349-5355.
J.-H. Kim, S. Fujita, S. Shiratori, "Design of a thin film for optical applications, consisting of high and low refractive index multilayers, fabricated by a layer-by-layer self-assembly method", Colloid Surf. Aspects 284-285 (2006) 290-294.
J.A. Hiller, J.D. Mendelsohn, M.F. Rubner, "Reversibly erasable nanoporous anti-reflection coatings from polyelectrolyte multilayers", Nat. Mater. 1 (2002) 59-63.
Meng et al., "Various shape memory effects of stimuli-responsive shape memory polymers", Smart Materials and Structures 2013, 22: 1-23.
Metwalli, E., et al. "Surface characterizations of mono-, di-, and tri-aminosilane treated glass substrates." Journal of colloid and interface science 298.2 (2006): 825-831.
Metzger et al., "Mechanical Properties of Mechanical Actuator for Treating Ischemic Stroke", Biomedical Microdevices 2002, 4:2: 89-96.
Mittleman, D. M.; et al. Optical Properties of Planar Colloidal Crystals: Dynamical Diffraction and the Scalar Wave Approximation. J. Chem. Phys. 1999, 111, 345-354.
Mohr, Gerhard J., Daniel Citterio, and Ursula E. Spichiger-Keller. "Development of chromogenic reactands for optical sensing of alcohols." Sensors and Actuators B: Chemical 49.3 (1998): 226-234.
Moirangthem, M.; et al. An Optical Sensor Based on a Photonic Polymer Film to Detect Calcium in Serum. Adv. Funct. Mater. 2016, 26, 1154-1160.
Munakata, et al., Three-dimensionally ordered macroporous polyimide composite membrane with controlled pore size for direct methanol fuel cells, Journal of Power Sources 2008, 178(2): 596-602.
Nam, H.; et al. Inkjet Printing Based Mono-Layered Photonic Crystal Patterning for Anti-Counterfeiting Structural Colors. Sci. Rep. 2016, 6, 30885.
Nguyen et al., "Modeling the Relaxation Mechanisms of Amorphous Shape Memory Polymers", M. L. Chambers, Adv. Mater. 2010, 22: 3411-3423.
Pan et al., "Response of inverse-opal hydrogels to alcohols", Journal of Materials Chemistry 2012, 22: 2018-2025.
Park, H. G.; et al. Electrically Driven Single-Cell Photonic Crystal Laser. Science 2004, 305, 1444-1447.

Park, Wounjhang; et al. "Mechanically tunable photonic crystal structure." Applied Physics Letters 85.21 (2004): 4845-4847.
Pfeiffer, Kristin, et al. "Antireflection coatings for strongly curved glass lenses by atomic layer deposition." Coatings 7.8 (2017): 118.
Pham, H. H.; et al. Multidye Nanostructured Material for Optical Data Storage and Security Data Encryption. Adv. Mater. 2004, 16, 516-520.
Phillips; et al "Biomimetic broadband antireflection gratings on solar-grade multicrystalline silicon wafers" Applied Physics Letters; Nov. 9, 2011, vol. 99, pp. 191103 (1)-(3).
Potyrailo et al., "Morpho butterfly wing scales demonstrate highly selective vapour response", Nature photonics 2007, 1: 123-128.
Quitmann et al., "Environmental Memory of Polymer Networks under Stress", Adv. Mater. 2014, 26: 3441-3444.
S. Degand, G. Lamblin, C.C. Dupont-Gillain, "Colloidal lithography using silica particles: Improved particle distribution and tunable wetting properties", J. Colloid Interf. Sci. 392 (2013) 219-225.
S. Lu,; et al. "Receptor-Ligand-Based Specific Cell Adhesion on Solid Surfaces: Hippocampal Neuronal Cells on Bilinker Functionalized Glass" Nano Lett. 6 (2006) 1977-1981.
S. Walheim, E. Schäffer, J. Mlynek, U. Steiner, "Nanophase-Separated Polymer Films as High-Performance Antireflection Coatings", Science 283 (1999) 520-522.
S.P. Pack, N.K. Kamisetty, M. Nonogawa, K.C. Devarayapalli, K. Ohtani, K. Yamada, Y. Yoshida, T. Kodaki, K. Makino, "Direct immobilization of DNA oligomers onto the amine-functionalized glass surface for DNA microarray fabrication through the activation-free reaction of oxanine", Nucleic Acids Res. 35 (2007), 10 pages.
Schäfer et al., "Fully Reversible Shape Transition of Soft Spheres in Elastomeric Polymer Opal Films", Langmuir 2013, 29: 11275-11283.
Schäfer et al., "Reversible Light-, Thermo-, and Mechano-Responsive Elastomeric Polymer Opal Films", Chemistry of Materials 2013, 25: 2309-2318.
Schneider, Friedrich. "The financial flows of transnational crime and tax fraud in OECD countries: What do we (not) know?." Public Finance Review 41.5 (2013): 677-707.
Small IV, et al., "Laser-activated shape memory polymer intravascular thrombectomy device", Optics Express 2005, 13: 8204-8213.
Stober, W.; et al. Controlled Growth of Monodisperse Silica Spheres in Micron Size Range. J. Colloid Interface Sci. 1968, 26, 62-69.
Stojilovic, N., Why Can't We See Hydrogen in X-Ray Photoelectron Spectroscopy? J. Chem. Edu. 2012, 89, 1331-1332.
Stuart et al., "Emerging applications of stimuli-responsive polymer materials", Nature Materials 2010, 9: 101-113.
Sun; et al. "Broadband moth-eye antireflection coatings on silicon" Applied Physics Letters; Feb. 14, 2008, vol. 92, pp. 061112 (1)-(3).
T. Lohmueller, M. Helgert, M. Sundermann, R. Brunner, J.P. Spatz, "Biomimetic Interfaces for High-Performance Optics in the Deep-UV Light Range", Nano Lett. 8 (2008) 1429-1433.
T. Xie, "Recent advances in polymer shape memory", Polymer 2011, 52: 4985-5000.
Takeoka et al., "Polymer Gels that Memorize Structures of Mesoscopically Sized Templates. Dynamic and Optical Nature of Periodic Ordered Mesoporous Chemical Gels", Langmuir 2002, 18: 5977-5980.
Tobushi et al., "Thermomechanical properties in a thin film of shape memory polymer of polyurethane series", Smart Mater. Struct. (1996) 5: 483-491.
Toor, F; et al. "Nanostructured silicon via metal assisted catalyzed etch (MACE): chemistry fundamentals and pattern engineering" Nanotechnology 2016, 27, 412003.
Tsai et al., "Retainment of pore connectivity in membranes prepared with vapor-induced phase separation", Journal of Membrane Science 2010, 362: 360-373.
U. Schulz, "Review of modern techniques to generate antireflective propoerties on thermoplastic polymers", Appl. Opt. 45 (2006) 1608-1618.
Zhang et al., Fabrication and bioseparation studies of adsorptive membranes/felts made from electrospun cellulose acetate nanofibers, Journal of Membrane Science 2008, 319(1-2):176-184.
Velev et al., "Porous silica via colloidal crystallization", Nature 1997, 389: 447-448.

(56) References Cited

OTHER PUBLICATIONS

Vlasov, Y. A.; et al. On-Chip Natural Assembly of Silicon Photonic Bandgap Crystals. Nature 2001, 414, 289-293.

W.L. Min, B. Jiang, P. Jiang, "Bioinspired Self-Cleaning Antireflection Coatings", Adv. Mater. 20 (2008) 3914-3918.

Wang, Zhen, et al. "Programmable, pattern-memorizing polymer surface." Advanced Materials 23.32 (2011): 3669-3673.

Weissman et al., "Thermally Switchable Periodicities and Diffraction from Mesoscopically Ordered Materials", Science 1996, 274: 959-960.

J.Q. Xi, M.F. Schubert, J.K. Kim, E.F. Schubert, M. Chen, S.-Y. Lin, LiuW, J.A. Smart, "Optical thin-film materials with low refractive index for broadband elimination of Fresnel reflection", Nat. Photon. 1 (2007) 176-179.

Jang et al., "Combining Pattern Instability and Shape-Memory Hysteresis for Phononic Switching", Nano Lett. 2009, 9, 5: 2113-2119.

Jiang et al., "Template-Directed Preparation of Macroporous Polymers with Oriented and Crystalline Arrays of Voids", J. Am. Chem. Soc. 1999, 121: 11630-11637.

Jiang, P.; et al. Single-Crystal Colloidal Multilayers of Controlled Thickness. Chem. Mater. 1999, 11, 2132-2140.

K. Askar, B.M. Phillips, X. Dou, J. Lopez, C. Smith, B. Jiang, P. Jiang, "Self-assembled nanoparticle antiglare coatings", Opt. Lett. 37 (2012) 4380-4382.

K.M. Yeung, W.C. Luk, K.C. Tam, C.Y. Kwong, M.A. Tsai, H.C. Kuo, A.M.C. Ng, A.B. Djurisic, "2-Step self-assembly method to fabricate broadband omnidirectional antireflection coating in large scale", Sol Energ Mater Sol C 95 (2011) 699-703.

Kang et al., "Broad-wavelength-range chemically tunable block-copolymer photonic gels", Nature Materials 2007, 6: 957-960.

Keller, K.; et al. Inkjet Printing of Multicolor Daylight Visible Opal Holography. Adv. Funct. Mater. 2018, 28, 1706903.

Kloxin et al., "Covalent adaptable networks: smart, reconfigurable and responsive network systems", Chem. Soc. Rev. 2013, 42: 7161-7173.

Kluhr et al., Partially Oxidized Macroporous Silicon: A Three-Dimensional Photonic Matrix for Microarray Applications, Advanced Materials 2006, 18(23): 3135-3139.

Kobatake; et al. "Rapid and reversible shape changes of molecular crystals on photoirradiation" vol. 446, Apr. 12, 2007, doi: 10.1038/nature05669, pp. 1-4.

Koerner et al., "Remotely actuated polymer nanocomposites—stress-recovery of carbon-nanotube-filled thermoplastic elastomers", nature materials 2004, 3: 115-120.

Kunzelman et al., "Shape memory polymers with built-in threshold temperature sensors", Journal of Materials Chemistry 2008, 18: 1082-1086.

Kuswandi; et al., "A Simple Visual Ethanol Biosensor Based on Alcohol Oxidase Immobilized onto Polyaniline Film for Halal Verification of Fermented Beverage Samples", Feb. 2014, Sensors, 14(2):2135-2149. (Year: 2014).

L. Ionov, "3D Microfabrication using Stimuli-Responsive Self-Folding Polymer Films", Polymer Reviews, 2013, 53: 92-107.

Lee, E.; et al. Bio-Inspired Responsive Polymer Pillar Arrays. MRS Commun. 2015, 5, 97-114.

Lee, J. N.; et al. Solvent Compatibility of Poly(Dimethylsiloxane)-Based Microfluidic Devices. Anal. Chem. 2003, 75, 6544-6554.

Lendlein et al., "Biodegradable, Elastic Shape-Memory Polymers for Potential Biomedical Applications", Science 2002, vol. 296: 1673-1676.

Zhang, G. G.; et al. Unusual Aspects of Supramolecular Networks: Plasticity to Elasticity, Ultrasoft Shape Memory, and Dynamic Mechanical Properties. Adv. Funct. Mater. 2016, 26, 931-937.

Lendlein, A.; et al. Shape-Memory Polymers. Angew. Chem. Int. Ed. 2002, 41, 2034-2057.

Leng et al., "Shape-Memory Polymers-A Class of Novel Smart Materials", MRS Bulletin 2009, 34: 848-855, www.mrs.org/bulletin.

Leng et al., "Synergic effect of carbon black and short carbon fiber on shape memory polymer actuation by electricity", Journal of Applied Physics 2008, 104: 1-4.

Leo, S. Y.; et al. Chromogenic Photonic Crystal Sensors Enabled by Multistimuli-Responsive Shape Memory Polymers. Small 2018, 14, 1703515.

Li, H. L.; et al. Superoleophilic and Superhydrophobic Inverse Opals for Oil Sensors. Adv. Funct. Mater. 2008, 18, 3258-3264.

Li, P.; et al. Novel Programmable Shape Memory Polystyrene Film: A Thermally Induced Beam-Power Splitter. Sci. Rep. 2017, 7, 44333.

Li, Y., et al. "Broadband near-infrared antireflection coatings fabricated by three-dimensional direct laser writing." Optics letters 43.2 (2018): 239-242.

Lishchuk, P; et al. "Photoacoustic characterization of nanowire arrays formed by metal-assisted chemical etching of crystalline silicon substrates with different doping level" ScienceDirect 2019, 131-136.

Liu et al., "Review of progress in shape-memory polymers", J. Mater. Chem., 2007, 17: 1543-1558.

Louette, P.; et al. Poly(Dimethyl Siloxane) (Pdms) Xps Reference Core Level and Energy Loss Spectra Surf. Sci. Spectra 2006, 12, 38-43.

Lv et al., "Shape-Memory Polymer in Response to Solution", Advanced Engineering Materials 2008, 10, No. 6: 592-595.

M. Ibn-Elhaj, M. Schadt, "Optical polymer thin films with isotropic and anisotropic nano-corrugated surface topologies", Nature 410 (2001) 796-799.

M. Kursawe, R. Anselmann, V. Hilarius, G. Pfaff, "Nano-Particles by Wet Chemical Processing in Commercial Applicaitons", J. Sol-Gel Sci. Technol. 33 (2005) 71-74.

M. Sakhuja, J. Son, L.K. Verma, H. Yang, C.S. Bhatia, A.J. Danner, "Omnidirectional study of nanostructured glass packaging for solar modules", Prog. Photovol. 22 (2014) 356-361.

M.F. Schubert, F.W. Mont, S. Chhajed, D.J. Poxson, J.K. Kim, E.F. Schubert, "Design of multilayer antireflection coatings made from co-sputtered and low-refractive-index materials by genetic algorithm", Opt. Exp. 16 (2008) 5290-5298.

M.G. Moharam, D.A. Pommet, E.B. Grann, T.K. Gaylord, "Stable implementation of the rigorous coupled-wave analysis for surface-relief gratings: enhanced transmittance matrix approach", J. Opt. Soc. Am. A 12 (1995) 1077-1086.

M.I. Dafinone, G. Feng, T. Brugarolas, K.E. Tettey, D. Lee, "Mechanical Reinforcement of Nanoparticle Thin Films Using Atomic Layer Deposition", ACS Nano 5 (2011) 5078-5087.

M.S. Park, J.K. Kim, "Porous Structures of Polymer Films Prepared by Spin Coating with Mixed Solvents under Humid Condition", Langmuir 22 (2006) 4594-4598.

Maitland et al., "Photothermal Properties of Shape Memory Polymer Micro-Actuators for Treating Stroke", Lasers in Surgery and Medicine (2002) 30:1-11.

Mao, D.; et al. Design of Nano-Opto-Mechanical Reconfigurable Photonic Integrated Circuit. J. Lightwave Technol. 2013, 31, 1660-1669.

Mason et al., "Correlation between bulk morphology and luminescence in porous silicon investigated by pore collapse resulting from drying", Thin Solid Films 2002, 406: 151-158.

Mather et al., "Shape Memory Polymer Research", Annu. Rev. Mater. Res. 2009. 39: 445-471.

Yang et al., "Macroporous photonic crystal-based vapor detectors created by doctor blade coating", Appl. Phys. Lett. 2011, 98: 1-3.

McDonald, J. C.; et al. Poly(Dimethylsiloxane) as a Material for Fabricating Microfluidic Devices. Acc. Chem. Res. 2002, 35, 491-499.

Meng et al., "A Brief Review of Stimulus-active Polymers Responsive to Thermal, Light, Magnetic, Electric, and Water/Solvent Stimuli", Journal of Intelligent Material Systems and Structures, vol. 21—Jun. 2010: 859-885.

Lv, Tong, et al. "Superhydrophobic surface with shape memory micro/nanostructure and its application in rewritable chip for droplet storage." ACS nano 10.10 (2016): 9379-9386.

(56) References Cited

OTHER PUBLICATIONS

Mata, Alvaro, Aaron J. Fleischman, and Shuvo Roy. "Characterization of polydimethylsiloxane (PDMS) properties for biomedical micro/nanosystems." Biomedical microdevices 7 (2005): 281-293.
Cai, Zhongyu, et al. "A photonic crystal protein hydrogel sensor for Candida albicans." Angewandte Chemie 127.44 (2015): 13228-13232.
Zhong, Kuo, et al. "Instantaneous, simple, and reversible revealing of invisible patterns encrypted in robust hollow sphere colloidal photonic crystals." Advanced Materials 30.25 (2018): 1707246.
Burgess, Ian B., et al. "Encoding complex wettability patterns in chemically functionalized 3D photonic crystals." Journal of the American Chemical Society 133.32 (2011): 12430-12432.
Fang, Yin, et al. "Reconfigurable photonic crystals enabled by multistimuli-responsive shape memory polymers possessing room temperature shape processability." ACS applied materials & interfaces 9.6 (2017): 5457-5467.
Fu, Qianqian, Biting Zhu, and Jianping Ge. "Hierarchically structured photonic crystals for integrated chemical separation and colorimetric detection." Nanoscale 9.7 (2017): 2457-2463.
Wu, Suli, et al. "Structural color patterns on paper fabricated by inkjet printer and their application in anticounterfeiting." The Journal of Physical Chemistry Letters 8.13 (2017): 2835-2841.
Gourevich, Ilya, et al. "Multidye nanostructured material for optical data storage and security labeling." Chemistry of materials 16.8 (2004): 1472-1479.
Zhao, Qian, et al. "Shape memory polymer network with thermally distinct elasticity and plasticity." Science advances 2.1 (2016): e1501297.
Heo, Yongjoon, et al. "Controlled insertion of planar defect in inverse opals for anticounterfeiting applications." ACS applied materials & interfaces 9.49 (2017): 43098-43104.
Hou, Jue, et al. "Four-Dimensional Screening Anti-Counterfeiting Pattern by Inkjet Printed Photonic Crystals." Chemistry—An Asian Journal 11.19 (2016): 2680-2685.
Hu, Haibo, et al. "Magnetically responsive photonic watermarks on banknotes." Journal of Materials Chemistry C 2.19 (2014): 3695-3702.
Hu, Haibo, et al. "Photonic anti-counterfeiting using structural colors derived from magnetic-responsive photonic crystals with double photonic bandgap heterostructures." Journal of Materials Chemistry 22.22 (2012): 11048-11053.
Zhao, Qian, H. Jerry Qi, and Tao Xie. "Recent progress in shape memory polymer: New behavior, enabling materials, and mechanistic understanding." Progress in Polymer Science 49 (2015): 79-120.
Meng, Yao, et al. "Patterned and iridescent plastics with 3D inverse opal structure for anticounterfeiting of the banknotes." Advanced Optical Materials 6.8 (2018): 1701351.
Meng, Zhipeng, et al. "Structurally colored polymer films with narrow stop band, high angle-dependence and good mechanical robustness for trademark anti-counterfeiting." Nanoscale 10.30 (2018): 14755-14762.
Moirangthem, Monali, et al. "Photonic shape memory polymer with stable multiple colors." ACS applied materials & interfaces 9.37 (2017): 32161-32167.
Peng, Chang-Yi, et al. "Flexible photonic crystal material for multiple anticounterfeiting applications." ACS applied materials & interfaces 10.11 (2018): 9858-9864.
Schauer, Senta, et al. "Tunable diffractive optical elements based on shape-memory polymers fabricated via hot embossing." ACS applied materials & interfaces 8.14 (2016): 9423-9430.
Shang, Shenglong, et al. "Fabrication of magnetic field induced structural colored films with tunable colors and its application on security materials." Journal of Colloid and Interface Science 485 (2017): 18-24.
Yunus, Sami, et al. "Diffusion of oligomers from polydimethylsiloxane stamps in microcontact printing: Surface analysis and possible application." Surface and Interface Analysis: An International Journal devoted to the development and application of techniques for the analysis of surfaces, interfaces and thin films 39.12-13 (2007): 922-925.
Wang, Mingsheng, and Yadong Yin. "Magnetically responsive nanostructures with tunable optical properties." Journal of the American Chemical Society 138.20 (2016): 6315-6323.
Yang, Dongpeng, et al. "Polymerization-Induced Colloidal Assembly and Photonic Crystal Multilayer for Coding and Decoding." Advanced Functional Materials 24.6 (2014): 817-825.
Kuznetsov, Arseniy I., et al. "Optically resonant dielectric nanostructures." Science 354.6314 (2016): aag2472.
Lee, Hye Soo, et al. "Colloidal photonic crystals toward structural color palettes for security materials." Chemistry of Materials 25.13 (2013): 2684-2690.
International Preliminary Report on Patentablitiy dated May 10, 2013 for PCT Patent Application No. PCT/US2011/057484.

* cited by examiner

INTRAOCULAR PRESSURE SENSING MATERIAL, DEVICES, AND USES THEREOF

CROSS-REFERENCE TO RELATED APPLICATION

This application is the 35 U.S.C. § 371 national stage application of PCT Application No. PCT/US2019/038193, filed Jun. 20, 2019, where the PCT claims priority to, and the benefit of, U.S. provisional application entitled "INTRAOCULAR PRESSURE SENSING MATERIAL, DEVICES, AND USES THEREOF" having Ser. No. 62/687,614, filed Jun. 20, 2018, both of which are herein incorporated by reference in their entireties.

STATEMENT REGARDING FEDERALLY SPONSORED RESEARCH

This invention was made with Government support under HDTRA-1-15-1-0022 awarded by the Department of Defense/Defense Threat Reduction Agency. The Government has certain rights in this invention.

BACKGROUND

Measurement of intraocular pressure is important for glaucoma and many eye diseases. Currently, indirect methods are used for measuring intraocular pressure which involve external contact to the eye. However, the results are variable based upon the corneal thickness and other structural differences in the wall of the eye. As such, there exists a need for improved eye monitoring devices and techniques.

SUMMARY

In embodiments of the present disclosure, disclosed herein are intraocular implants. Intraocular implants as described herein can comprise a pressure-responsive material, the pressure-responsive material comprising chromogenic photonic crystals, wherein the chromogenic photonic crystals change confirmation resulting in a change of color of the pressure-responsive material in response to an amount of pressure exerted on the shape-memory chromogenic photonic crystals.

In embodiments according to the present disclosure, the pressure-responsive material can be a first color at a normal physiologic intraocular pressure of about 10 to about 20 mm Hg. The pressure-responsive material can be second color at an elevated intraocular pressure of greater than about 20 mm Hg. The pressure-responsive material can be a third color at a reduced intraocular pressure of less than about 10 mm Hg.

In embodiments according to the present disclosure, the implant can be an intraocular lens. In embodiments according to the present disclosure, the implant can be a glaucoma drainage device.

In embodiments according to the present disclosure, the pressure responsive material can be coated on a surface of a drainage tube of the glaucoma drainage device.

In embodiments according to the present disclosure, the surface can be an outer surface of the drainage tube. In embodiments according to the present disclosure, the surface can be an inner surface of the drainage tube.

In embodiments according to the present disclosure, the implant can comprise one or more layers of the pressure-responsive material coated on all or part of a surface of the implant or component thereof.

In embodiments according to the present disclosure, each of the one or more layers is about 0.5 mm to about 3 mm thick.

In embodiments according to the present disclosure, the pressure-responsive material can be integrated with a component of the implant.

In embodiments according to the present disclosure, the implant can comprise one or more layers of the pressure-responsive material embedded in all or part of a surface of the implant or component thereof. In other embodiments, the implant can include the pressure-responsive material in the body of the implant.

In embodiments according to the present disclosure, the pressure responsive material can comprise photonic crystals embedded in (e.g. encapsulated in) a hydrogel.

Also described herein are methods. In embodiments according to the present disclosure, methods as described herein comprise: implanting into the eye of a subject in need thereof an implant according to the present disclosure.

In embodiments according to the present disclosure, methods can further comprise detecting the color of the pressure-responsive material of the implant without contacting the eye.

In embodiments according to the present disclosure, methods can further comprise quantitatively measuring the color of the pressure-responsive material of the implant using a spectrometer.

In embodiments according to the present disclosure, a subject in need thereof can be a human or a canine. In embodiments according to the present disclosure, the subject in need thereof has or is at risk for ocular hypertension. In embodiments according to the present disclosure, the subject in need thereof has glaucoma.

In embodiments according to the present disclosure, a method of measuring intraocular pressure in a subject having an implant is described herein, the method comprising: detecting the color of the pressure-responsive material of the implant without contacting the eye. The subject can be a human or a canine. The subject can have ocular hypertension or can be at risk for ocular hypertension. The subject in need thereof can have glaucoma.

In embodiments according to the present disclosure, methods as described herein can comprise quantitatively measuring the color of the pressure-responsive material of the implant using a spectrometer or other spectral monitoring device, for example a smartphone with an application configured for spectrometry.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Definitions

As used herein, "about," "approximately," and the like, when used in connection with a numerical variable, can generally refers to the value of the variable and to all values of the variable that are within the experimental error (e.g., within the 95% confidence interval for the mean) or within +/−10% of the indicated value, whichever is greater.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as abnormal eye pressure and/or diseases and conditions associated with abnormal eye pressure (including but not limited to glaucoma). The effect can be therapeutic in terms of a partial or complete cure of a disease, condition, symptom or adverse effect attributed to the disease, disorder, or condition. The term "treatment" as used herein covers any treatment of glaucoma, ocular hypertension (elevated intraocular eye pressure), or reduced intraocular eye pressure, in a subject, particularly a human or a canine, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

Discussion

Measurement of intraocular pressure is important for diagnosis and treatment of glaucoma and many other eye diseases. Currently, indirect methods are used for measuring intraocular eye pressure. These methods involve external eye contact to the eye. Thus, current methodologies produce results that are variable and based upon the corneal thickness and other structural differences in the wall in the eye that can change over time. As such, current methodologies can produce inaccurate results which can negatively impact eye health evaluations and disease monitoring and treatment.

With that said, described herein are materials, which can be biocompatible, that can be pressure-responsive and incorporated in intraocular lenses and/or other eye devices that can be capable of monitoring eye pressure. The materials can be capable of changing color in response to pressure exerted on the material. The color of the material can be quantitatively measured and can provide a direct and non-contact method of measuring intraocular pressure. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Described herein are devices that can be implanted into a subject, such as in the eye or eye region, that can include a pressure-responsive material. The pressure responsive material can be composed of chromogenic photonic crystals that can be based on smart shape memory polymers. The chromogenic photonic crystals can be as described in Leo, S. et al. 2018. Chromogenic Photonic Crystal Sensors Enabled by Multistimuli-Responsive Shape Memory Polymers" Small 14(12):1703515, which is incorporated by reference as if fully set forth herein. In embodiments according to the present disclosure, chromogenic photonic crystal sensors are based on smart shape memory polymers (SMPs) comprising polyester/polyether-based urethane acrylates blended with tripropylene glycol diacrylate, which exhibit nontraditional all-room-temperature shape memory (SM) effects.

The pressure-responsive material can change color when different pressures are exerted on it. Thus, when incorporated in a device that is implanted into an eye, the intraocular pressure can be exerted on the pressure-responsive material incorporated in the device. The pressure-responsive material can change confirmation depending on the amount of pressure exerted on it by the eye contents and thus be a particular color depending on that exerted pressure. The color can be qualitatively measured by shining a light into the eye and onto the pressure-responsive material implanted in the eye and observing the color of the pressure-responsive material. The color can be measured quantitatively using spectral analysis to determine the color of the pressure-responsive material. Any suitable device that can externally measure the color spectrally can be used. In some aspects, the device is a hand held spectrometer or smartphone with an imaging device. Such devices are generally known and available. For example, a color analysis app (e.g., Color Mate Version 1.2.2) installed on a smartphone can be used in analyzing the RGB values of the sensor in response to different intraocular pressures.

The color of the pressure-responsive material can be tuned by including silica particles with different diameters. Experiments have confirmed that the pressure-responsive materials of the present disclosure and devices including the pressure-responsive material can cover the whole visible spectrum range from 400 to 700 nm. For example, by including silica particles having an average diameter of about 500 to 500 nm, about 400 to 450 nm, and about 600 to 650 nm in the same pressure-responsive material, the material can appear green, blue, and red, respectively. The visible color can correlate to a pressure.

The color of the pressure-responsive material can be directly correlated to the intraocular pressure. In some aspects, at normal physiologic intraocular pressure (about 10 to about 20 mm Hg) the color of the pressure-responsive material can range from about 500 nm to 550 nm corresponding to a green color. The color of the pressure-responsive material can range be a first color. An intraocular pressure that is above normal (elevated intraocular eye pressure) can be anything over about 20 mm Hg. At elevated intraocular pressures ranging from about 20 mm Hg to about 30 mm Hg or more, the color of the pressure-responsive material can be a second color that is different from that at normal physiological pressure. The color of the pressure-responsive material can range from about 400 nm to 450 nm corresponding to a blue color. If a subject is not having symptoms of an eye disease such as glaucoma but has an elevated intraocular pressure, this can be referred to as ocular hypertension. These individuals are at risk for developing an eye disease, such as glaucoma, and can require more intensive monitoring.

Ocular hypertension is not the only pressure abnormality that can lead to eye problems. In some cases, such as after eye surgery (e.g. glaucoma surgery) or episodes of ocular ischemia, the intraocular pressure can become too low. A condition called hypotony can be diagnosed if the intraocular pressure decreases to about 6 mm Hg or less or in some cases about 10 mm Hg or less. When intraocular pressure is too low it can cause distortions of the retina, lens, and cornea that can degrade vision and lead to vision loss. At reduced intraocular pressures ranging from about 4 mm Hg to about 10 mm Hg, the color of the pressure-responsive material can be a third color that is different than the color at normal physiological pressure or elevated pressure. The color of the pressure-responsive material can range from about 600 nm to 650 nm corresponding to a red color.

As described above, the pressure-responsive material can be coated in one or more layers on or incorporated into at least a portion of an implantable intraocular device. The pressure-responsive material can be coated on or incorporated into at least a portion of an intraocular lens or other prosthetic devices. In some aspects, a layer of the pressure-responsive material can range from about 0.1 mm to 0.5 mm, 0.5 mm to about 3 mm, about 1 mm to about 2.5 mm, about 1.5 mm to about 2 mm thick. Suitable intraocular lenses and prosthetics are generally known and available.

The implantable device can include the pressure-responsive material in the body of the implant. In the case of an intra-ocular lens implant, for example, the pressure-responsive material could be placed in the outer part of the optic, thus leaving the central visual axis clear of any color change or potentially different refractive index material to prevent or minimize visual clarity issues while still undergoing pressure-responsive color change.

Glaucoma can be treated by implanting a device that helps keep the surgically-created drainage opening from healing and closing down. Many incorporate a tube through which the aqueous eye fluid passes. Others are solid and promote the flow of fluid along the surface of the implant. Newer implants commonly referred to as micro-invasive glaucoma surgery devices are tiny drainage implants (e.g. the Cypass Microstent from Alcon, AqueSys's XEN Gel Stent, MicroShunt Glaucoma Drainage System by InnFocus Inc., STARflo Glaucoma Implant and MINIject from iSTar Madical SA, and the Hydrus Microstent form Ivantis) have also been developed and incorporate tiny drainage conduits (e.g. stents) that can create a permanent conduits for moving eye fluids and decreasing intraocular pressure. Other various implants for treatment of glaucoma are known. The pressure-responsive material can be coated on or incorporated in any of the components of an implant for treatment of glaucoma. In some aspects the pressures-responsive material can be incorporated on or on the inside of the drainage stent or tube of the implant.

In use, the pressure-responsive material can be coated on an existing eye implant device described above. In other aspects, the pressure-responsive material can be coated on or otherwise incorporated in an eye implant device at the point of manufacture of the device or any of its components or material. The eye implant device can be inserted into an eye of a subject using any suitable surgical technique that is appropriate for that particular eye implant and subject. This can be determined by the medical practitioner. After implantation, the pressure of the subject's eye containing the eye implant device can be measured qualitatively by viewing the color of the pressure-responsive material using suitable eye examination devices and equipment (e.g. ophthalmoscope, ophthalmic lope, otoscopes, etc.) and/or qualitatively by using a suitable spectrophotometer device. These are discussed elsewhere herein. The method of pressure measurement when the pressure-responsive material and devices incorporating the pressure-responsive material is employed does not require contact with the eye or subject to changes in the structures of the eye. Further, this measurement method does not require any eye dilation or other uncomfortable procedures to allow measurement. Further, the devices herein allow for measurement of eye pressure at any time. This can be an advantage of current techniques as the pressure of the eye can change throughout the day. The devices and techniques described herein can thus allow for improved monitoring of the eye, particularly a diseased eye, and improve care of the subject.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An intraocular implant comprising:
   a pressure-responsive material, the pressure-responsive material comprising chromogenic photonic crystals, wherein the chromogenic photonic crystals change conformation resulting in a change of color of the pressure-responsive material in response to an amount of pressure exerted on the shape-memory chromogenic photonic crystals and wherein the chromogenic photonic crystal comprise smart shape memory polymers (SMPs), the SMPs comprising polyester/polyether-based urethane acrylates blended with tripropylene glycol diacrylate, wherein the implant is an intraocular lens.

2. The intraocular implant of claim 1, wherein the pressure-responsive material is a first color at a normal physiologic intraocular pressure of about 10 to about 20 mm Hg, wherein the first color ranges from about 500 nm to 550 nm corresponding to a green color.

3. The intraocular implant of claim 2, wherein the pressure-responsive material is a second color at an elevated intraocular pressure of greater than about 20 mm Hg, wherein the second color ranges from about 400 nm to 450 nm corresponding to a blue color.

4. The intraocular implant of claim 3, wherein the pressure-responsive material is a third color at a reduced intraocular pressure of less than about 10 mm Hg, wherein the third color ranges from about 600 nm to 650 nm corresponding to a red color.

5. A method comprising:
   implanting into the eye of a subject in need thereof an implant as in claim 1, wherein the subject in need thereof is a human or a canine.

6. The method of claim 5, further comprising detecting the color of the pressure-responsive material of the implant without contacting the eye and quantitatively measuring the color of the pressure-responsive material of the implant using a spectrometer.

7. The method of claim 5, wherein the subject in need thereof has or is at risk for ocular hypertension or wherein the subject in need thereof has glaucoma.

8. A method of measuring intraocular pressure in a subject having an implant as in claim 1, the method comprising:
   detecting the color of the pressure-responsive material of the implant without contacting the eye.

9. The method of claim 8, wherein the subject is a human or a canine, and wherein the subject has or is at risk for ocular hypertension or wherein the subject in need thereof has glaucoma.

10. The method of claim 8, further comprising quantitatively measuring the color of the pressure-responsive material of the implant using a spectrometer.

11. An intraocular implant comprising:
    a pressure-responsive material, the pressure-responsive material comprising chromogenic photonic crystals, wherein the chromogenic photonic crystals change conformation resulting in a change of color of the pressure-responsive material in response to an amount of pressure exerted on the shape-memory chromogenic photonic crystals and wherein the chromogenic photonic crystal comprise smart shape memory polymers (SMPs), the SMPs comprising polyester/polyether-based urethane acrylates blended with tripropylene glycol diacrylate, wherein the implant is a glaucoma drainage device.

12. The intraocular implant of claim 11, wherein the pressure responsive material is coated on a surface of a drainage tube of the glaucoma drainage device.

13. The intraocular implant of claim 12, wherein the surface is an outer surface of the drainage tube.

14. The intraocular implant of claim 12, wherein the surface is an inner surface of the drainage tube.

15. An intraocular implant comprising:
    a pressure-responsive material, the pressure-responsive material comprising chromogenic photonic crystals, wherein the chromogenic photonic crystals change conformation resulting in a change of color of the pressure-responsive material in response to an amount of pressure exerted on the shape-memory chromogenic photonic crystals and wherein the chromogenic photonic crystal comprise smart shape memory polymers (SMPs), the SMPs comprising polyester/polyether-based urethane acrylates blended with tripropylene glycol diacrylate, wherein the implant comprises one or more layers of the pressure-responsive material embedded in all or part of a surface of the implant or component thereof.

16. An intraocular implant comprising:
    a pressure-responsive material, the pressure-responsive material comprising chromogenic photonic crystals, wherein the chromogenic photonic crystals change conformation resulting in a change of color of the pressure-responsive material in response to an amount of pressure exerted on the shape-memory chromogenic photonic crystals and wherein the chromogenic photonic crystal comprise smart shape memory polymers (SMPs), the SMPs comprising polyester/polyether-based urethane acrylates blended with tripropylene glycol diacrylate, wherein the implant comprises one or more layers of the pressure-responsive material coated on all or part of a surface of the implant or component thereof.

17. The intraocular implant of claim 16, wherein each of the one or more layers is about 0.5 mm to about 3 mm thick.

18. An intraocular implant comprising:
    a pressure-responsive material, the pressure-responsive material comprising chromogenic photonic crystals, wherein the chromogenic photonic crystals change conformation resulting in a change of color of the pressure-responsive material in response to an amount of pressure exerted on the shape-memory chromogenic photonic crystals and wherein the chromogenic photonic crystal comprise smart shape memory polymers (SMPs), the SMPs comprising polyester/polyether-based urethane acrylates blended with tripropylene glycol diacrylate, wherein the pressure-responsive material is integrated with a component of the implant.

19. An intraocular implant comprising:

a pressure-responsive material, the pressure-responsive material comprising chromogenic photonic crystals, wherein the chromogenic photonic crystals change conformation resulting in a change of color of the pressure-responsive material in response to an amount of pressure exerted on the shape-memory chromogenic photonic crystals and wherein the chromogenic photonic crystal comprise smart shape memory polymers (SMPs), the SMPs comprising polyester/polyether-based urethane acrylates blended with tripropylene glycol diacrylate, wherein the pressure-responsive material comprises a hydrogel.

\* \* \* \* \*